United States Patent
Joachimsthaler et al.

(10) Patent No.: US 6,976,490 B2
(45) Date of Patent: Dec. 20, 2005

(54) THERAPEUTIC SINGLE DOSE GAS ADMINISTRATION SYSTEM

(75) Inventors: Brian D. Joachimsthaler, Collinsville, IL (US); William C. Dean, Valley Park, MO (US); Robert E. Sever, Florissant, MO (US)

(73) Assignee: Essex Manufacturing Company, St. Louis, MO (US)

( * ) Notice: Subject to any disclaimer, the term of this patent is extended or adjusted under 35 U.S.C. 154(b) by 104 days.

(21) Appl. No.: 10/315,367

(22) Filed: Dec. 10, 2002

(65) Prior Publication Data

US 2004/0107966 A1 Jun. 10, 2004

(51) Int. Cl.[7] ............................................. A62B 9/02
(52) U.S. Cl. ......................... 128/204.26; 128/205.24; 128/201.28
(58) Field of Search ...................... 128/204.26, 205.24, 128/201.28, 205.18; 137/385, 505; 251/95; 239/533.15

(56) References Cited

U.S. PATENT DOCUMENTS

| | | | | |
|---|---|---|---|---|
| 4,173,986 A | * | 11/1979 | Martin | 137/613 |
| 4,197,842 A | * | 4/1980 | Anderson | 128/203.12 |
| 4,250,876 A | * | 2/1981 | Kranz | 128/202.22 |
| 4,946,130 A | * | 8/1990 | Kooiman | 251/95 |
| 5,026,026 A | * | 6/1991 | Sever et al. | 251/230 |
| 5,411,059 A | * | 5/1995 | Sever et al. | 137/599.04 |
| 5,429,123 A | * | 7/1995 | Shaffer et al. | 128/204.23 |
| 5,529,058 A | * | 6/1996 | Crippen | 128/201.28 |
| 5,771,878 A | * | 6/1998 | Lewis et al. | 126/42 |
| 5,823,023 A | * | 10/1998 | Benda | 70/180 |
| 6,260,819 B1 | * | 7/2001 | Ovsepyan | 251/96 |
| 6,481,437 B1 | * | 11/2002 | Pate | 128/203.26 |
| D468,012 S | * | 12/2002 | Shirley et al. | D24/110.6 |
| 6,551,279 B1 | * | 4/2003 | Hyun | 604/132 |
| 6,568,437 B2 | * | 5/2003 | Dean et al. | 141/97 |
| 6,604,523 B2 | * | 8/2003 | Lurie et al. | 128/205.24 |
| 6,644,313 B2 | * | 11/2003 | Prime et al. | 128/205.24 |
| 6,647,982 B1 | * | 11/2003 | Zaiser et al. | 128/204.18 |

* cited by examiner

Primary Examiner—Henry Bennett
Assistant Examiner—Amanda Wieker
(74) Attorney, Agent, or Firm—Peter S. Gilster; Greensfelder, Hemker & Gale, P.C.

(57) ABSTRACT

A system (A) for providing single continuous dose of a gaseous heliox mixture to a patient with breathing difficulty includes a device (1) providing a constant and continuous flow of the heliox mixture, and a gas storage tank (2) for the mixture. A flow control is selectively operated to initiate flow of the heliox to the patient. It has a locking mechanism to prevent it from being turned off after the flow begins. The regulator can be reset for reuse by a service entity.

18 Claims, 8 Drawing Sheets

THERAPEUTIC SINGLE DOSE GAS ADMINISTRATION SYSTEM

BACKGROUND OF THE INVENTION

1. Field of the Invention

The present invention relates to a system for administering a gaseous mixture in a single continuous dose to a patient for medical treatment. More specifically, this invention relates to a device for administering a single dose of gas to a patient by means of a control valve that once turned to the "on" position cannot be turned to the "off" position by the patient.

2. Known Art

In the treatment of patients with asthma it has been discovered that a gaseous mixture of helium and oxygen, referred to herein as a "heliox" mixture, is therapeutically beneficial. During an asthmatic attack, the bronchioles of the lungs become constricted and blocked with mucus. This constriction and subsequent blockage of the bronchioles causes the patient suffering the attack to be deprived of oxygen which can lead to discomfort, brain damage, or even death if not treated. It has been discovered that a heliox mixture consisting solely of helium and oxygen (usually about 80% helium and about 20% oxygen) will help increase the oxygen absorption into the restricted and blocked bronchioles of the lungs. Garret U.S. Pat. No. 6,001,332 contends that because the density of helium is lower than that of oxygen, a heliox mixture is more readily absorbed by restricted bronchioles than pure oxygen. It is believed that when oxygen is mixed with helium in a heliox mixture, the mixture of the gasses will allow more oxygen to enter the lungs and alleviate a severe asthmatic attack.

Despite heliox treatment's properties to increase oxygen absorption of the lungs there remains a potential problem when using heliox. After a patient has begun a heliox treatment the symptoms of the asthmatic attack cease or are reduced almost immediately. This causes the patient to feel as if the treatment is no longer needed and the patient or other person treating the patient (usually an Emergency Medical Technician or another person assisting the patient) may discontinue the treatment by shutting off the device that supplies the treatment. When this is done the sudden absence of helium from the patient causes the return of an acute asthmatic attack, in that while the bronchioles were able to absorb more oxygen with the heliox mixture, they are still in a contracted and blocked state. The sudden removal of helium from the patient's lungs may cause the patient to lapse into an acute asthmatic attack, the severity of which may be fatal. Thus, in order for a heliox treatment to be effective, it should be administered continuously in a single dose until a qualified medical specialist can determine that the heliox is no longer needed or that other treatment may be safely administered.

There are known regulators available for administering a heliox treatment, or other gaseous treatment to patients. These known devices typically have the drawback that either the patient or another person assisting the patient has complete control of the ability to turn the regulators on or off or to adjust flow rate. For example, Lewis U.S. Pat. No. 6,302,106 contends a system designed to be adaptable for use with a heliox mixture, the regulation being readily adjustable to vary the flow rates of dispensing of the gaseous mixture. Also, pending published application U.S. application 200010035183 to Hill filed on Nov. 1, 2001, provides for a system of ventilation with a maximum degree of flexibility allowing the system to be turned on or off if desired.

While in certain situations the ability to vary the flow rate of the gaseous mixture to the patient may be desirable, this is believed to be undesirable for patients receiving a heliox treatment who are suffering from an acute asthmatic attack as mentioned above, if the heliox treatment is suddenly stopped by the patient who feels it is safe to do so, the sudden lack of or reduction of heliox treatment might cause the patient to relapse into serious asthmatic attack. There exists a need then in the art of breathing regulators and gas distribution systems that prevents a patient from discontinuing or altering the flow rate of the life saving treatment of heliox, and provides a heliox treatment in a safe, single, continuous dose.

SUMMARY OF THE PRESENT INVENTION

Among the objects, advantages and features of the present invention are the provision of an improved gas regulation system and device which prevents the user from turning the device off and which provides a single dose of continuous treatment of a gaseous mixture. In a preferred embodiment explained herein below, the mixture used is a heliox mixture comprising about 80% helium to about 20% oxygen without other gas constituents. Among other objects, advantages, and features of this system is such a device that provides a therapeutic gaseous heliox mixture in a safe, single dose, at a continuous flow; that is of high quality and of a reliable nature; that can be packed in a sterile tamper-resistant container; that is capable of handling a variety of different gaseous mixtures at varying pressures; that cannot be activated by accident; and that can be reset and reused; and that is capable of being easily reset by a specialized tool for further use and recharged by an authorized entity. It is further an object of this invention to provide a method for treating breathing difficulty that comprises the steps of connecting a means for delivering the to the patient a beneficial gaseous mixture from the device to the patient, turning a flow control apparatus until it is locked in a "on" position, and then leaving the apparatus in the "on" position until all the gaseous mixture has been delivered to the patient or the patient has seen a qualified medical professional.

Briefly, the system comprises a regulator including a flow initiation control operable by the patient to initiate the flow of a gaseous mixture from a pressure vessel which is connected to a regulator. A lock on the regulator prevents the control from being turned to the "off" position once activated. A specialized tool is provided to allow the regulator to be reset after it has been used, so that the system and be recharged and reset.

Additional objects, advantages and novel features of the invention will be set forth in the following description.

The term gaseous mixture when used in this application generally is meant to include any suitable and type of gas or liquid that is in a gaseous state once released from the pressurized container.

BRIEF DESCRIPTION OF THE DRAWINGS

Corresponding elements are identified by corresponding reference characters throughout the views.

DETAILED DESCRIPTION OF A PRACTICAL EMBODIMENT

Figure 1:
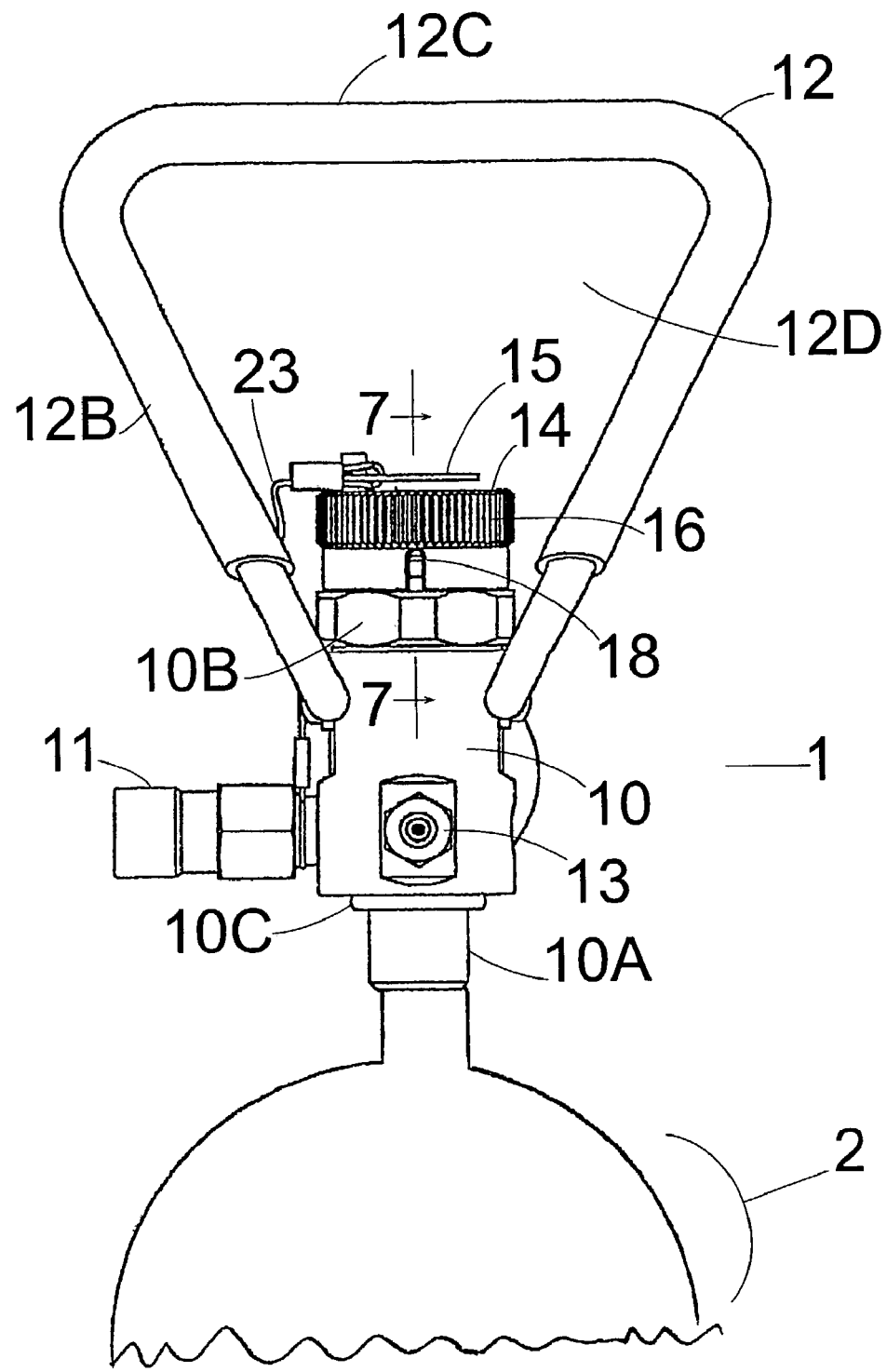
FIG. 1 is a perspective view of an improved gas administration system of the present invention.

FIG. 1 shows a system A of the invention in its entirety with the exception of a special resetting tool which is described below. The system is designed to provide a patient having breathing difficulty with a single dose of an easily breathable gaseous mixture comprised of about 80% helium to 20% oxygen (the mixture being herein called "heliox"). The system can then be reset and refilled after use. System A comprises as basic components a regulator 1, a gas storage tank 2, and a resetting tool 3 (see FIGS. 1 and 8).

Regulator 1 includes a body 10 having a handle 12 for carrying the system. Regulator 10 is connected to a gas storage tank 2 by a regulator body fitting 10A. The tank is preferably of size "D" so as to hold enough heliox as supplied to a patient in a continuous dose to enable the patient to arrive at a treatment center such as a hospital where more permanent treatment can be administered. A resetting tool 3 mentioned above is usable to reset regulator 1 after use and is discussed in greater detail below.

Figure 2:
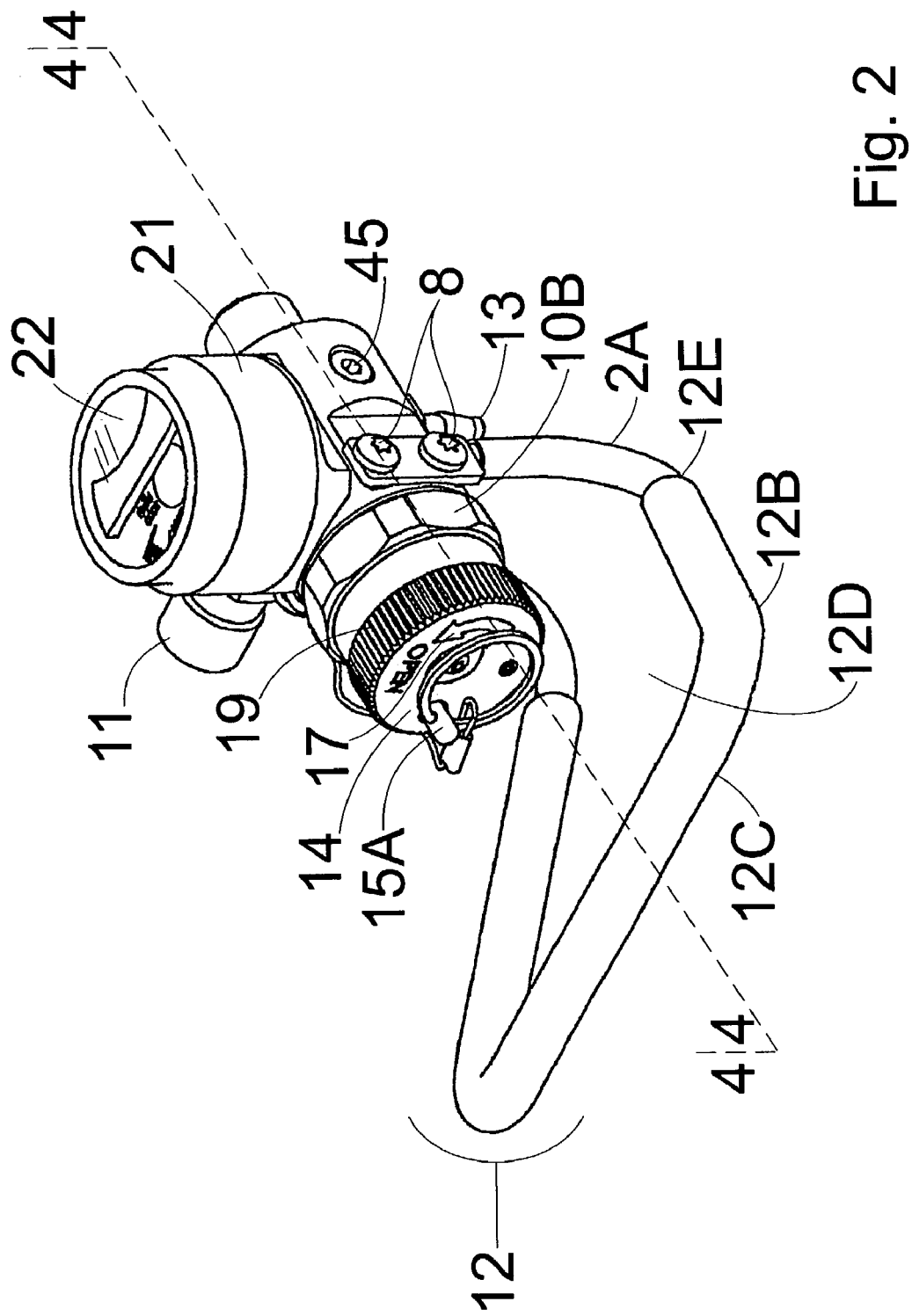
FIG. 2 is a perspective view of the regulator.

As shown in FIGS. 1 and 2, the regulator comprises a body 10 of brass alloy. Substantially all components of body 10 are constructed of brass except as otherwise noted.

Extending outwardly from body 10 perpendicular to its vertical axis are a fill fitting 11 and a fitting assembly 13, both of which are constructed of brass alloy. Fill fitting 11 is for filling tank 2 with heliox mixture and fitting assembly 13 is for connecting tubing for supplying the patient with a dose of heliox. Extruding outwardly from one side of body 10 is a pressure gauge 21 for showing the pressure of the heliox mixture in tank 2.

A gauge protector 22 protects pressure gauge 21 from external damage. The gauge protector may be of the design configuration described in co-assigned U.S. Design patent application Ser. No. 29/153,112 filed Nov. 9, 2001, and incorporated herein by reference.

Body 10 is also encircled by a hex ring 10B which is constructed of an aluminum alloy and secures together body 10 and a cap 41 of the body, as described below.

Fill fitting 11 is configured to receive a known type of filling connection (not shown) for refilling tank 2 with the heliox mixture by an authorized service entity, enabling system A to be used multiple times. Fitting outlet assembly 13 permits the heliox to exit regulator 1 and then be delivered by a tubing 13T to the patient.

Figure 4:
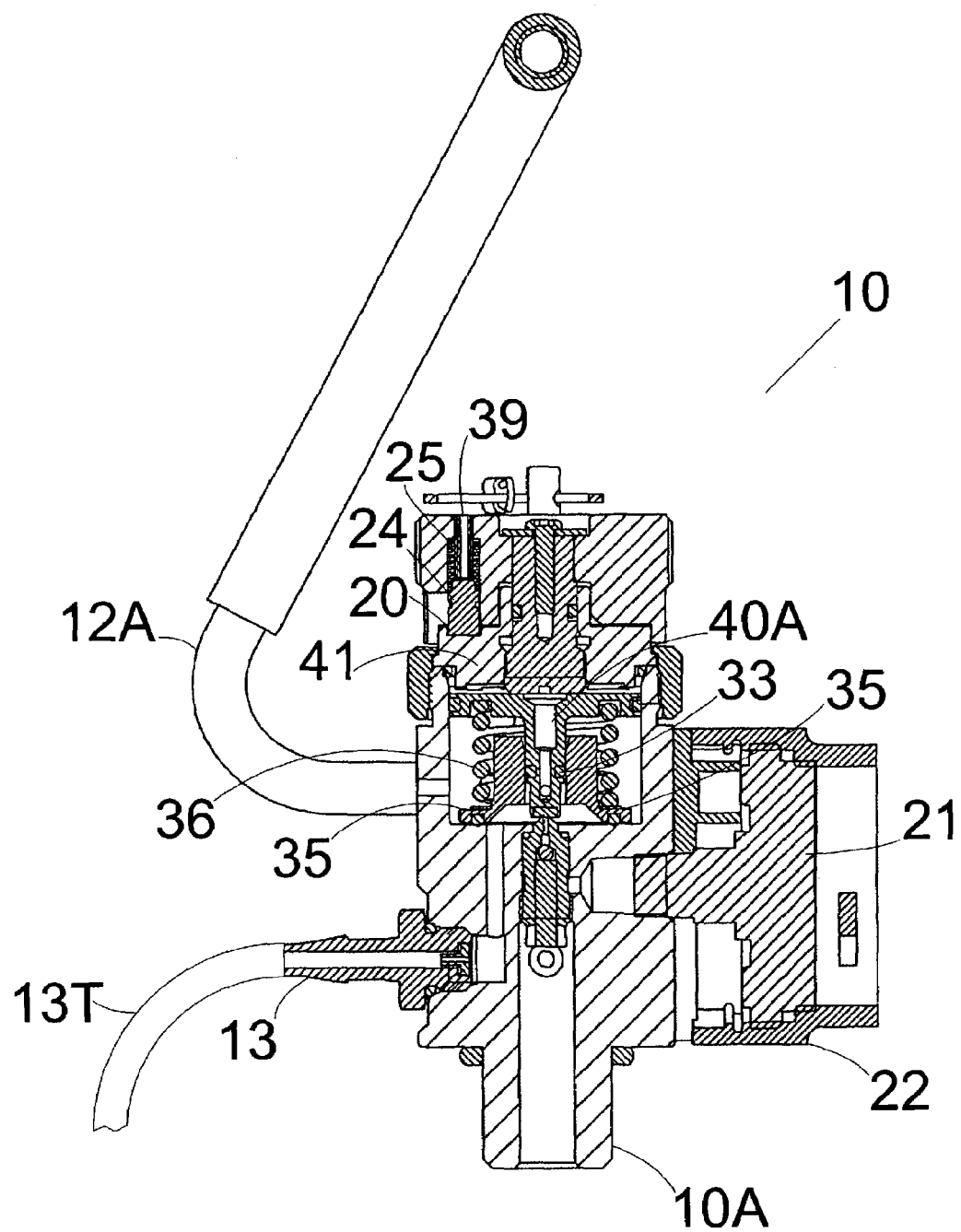
FIG. 4 is a vertical cross sectional view taken along line 4—4 of FIG. 2.

Assembly 13 can deliver the gaseous mixture to one or more users at one time as by connecting more than one breathing tube connection to body 10 allowing for a single or double outlet device. One such fitting outlet assembly is shown in FIGS. 2 and 4, but multiple such assemblies can be used (as in FIG. 8) for dispensing heliox to multiple patients.

At 45 is a rupture kit assembly for high pressure protection. Rupture kit 45 provides an emergency gas discharge outlet permitting the gas to escape if the pressure in tank 2 is too high, as in the event of an overpressure caused by a fire for example. The pressure at which gas could escape through rupture kit 45 is pre-determined according to known minimum save levels.

The preferred gaseous mixture of heliox comprises about 80% helium to about 20% oxygen and provides therapeutic relief for asthma sufferers and other patients having comparable breathing difficulties or symptoms. Connector fitting 10A is encircled by an o-ring 10C at its upper end to provide an air-tight seal between regulator 1 and tank 2.

Body 10 with tank 2 attached is carried by handle 12. Handle 12 has portions coated with a soft resilient polymer 12E, such as results from being dipped in brown vinyl, this color being universally recognized in the art of breathing regulators to signify a device containing heliox rather than another gas. Handle 12 has a horizontal grip 12C, a pair of opposed oblique side members 12B, two lateral side portions 12A, and space 12D. Grip 12C is located well above body 10 to provide space 12D of ample proportion for operating the device. The two oblique side members 12B converge toward body 10 and extend into respective side portions 12A which approach body 10 horizontally and are secured to body 10 by one or more Torx® screws 8 or their equivalent on opposing sides of body 10.

Figure 3:
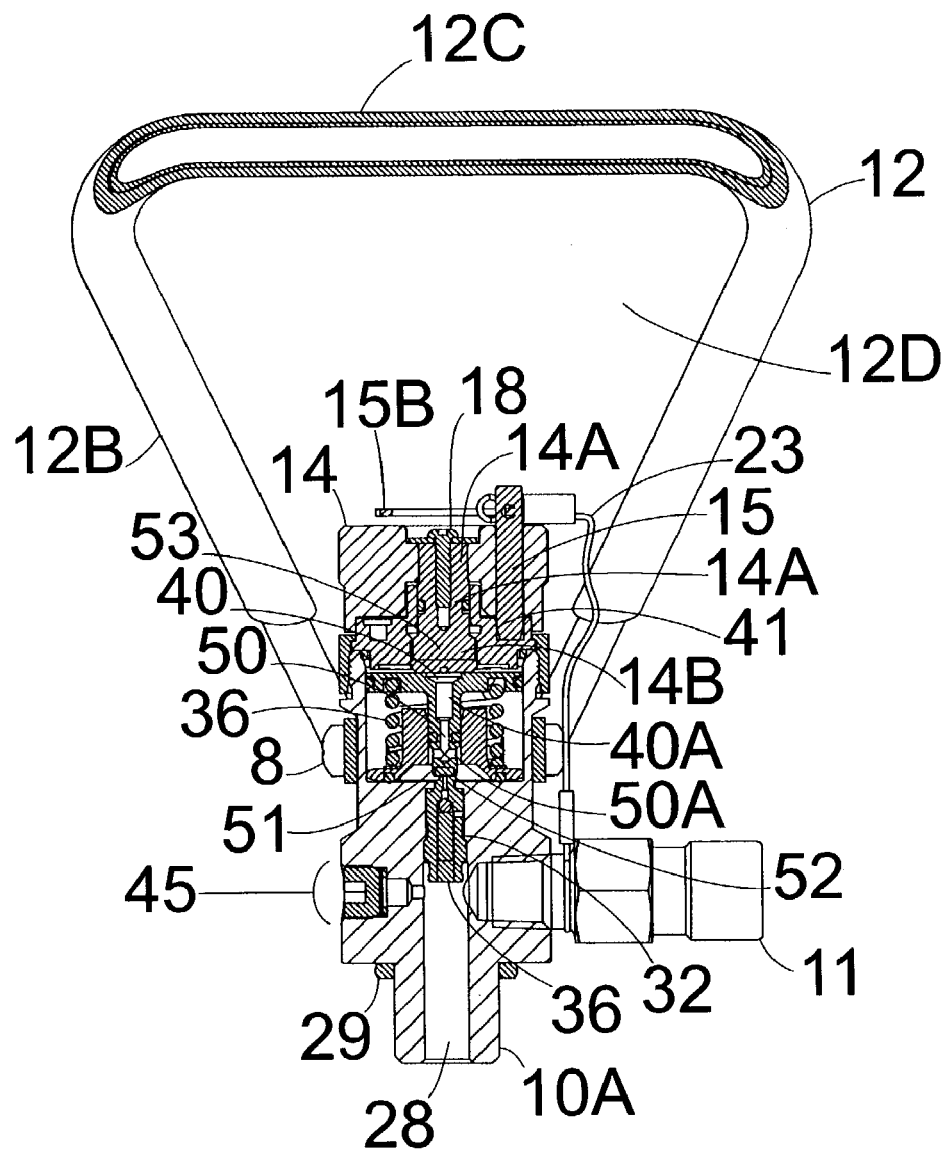
FIG. 3 is a vertical cross sectional view taken along line 3—3 of FIG. 1.

Referring to FIGS. 3 and 4, a notable operating circular flow control knob 14 of polypropylene sits atop body 10. Other devices such as levers or knobs of various configurations can be used in place of a knob if desired. Knob 14 extends upwardly from cap 41. As the cross-sectional view shows, body 10 contains a piston assembly 40 beneath cap 41. The assembly includes a piston 40A, and a compression spring 36 beneath the piston. The piston has a hollow stem 50 carrying at its lower end a seal 52 designed to prevent heliox from entering regulator 10 until the patient or user desires, and as long as knob 14 is in the "off" position. However, hollow stem 50 also allows heliox to enter the regulator body 10 at a regulated pressure when knob 14 is in the "on" position. These devices provide pressure regulation and flow control of the heliox mixture.

Knob 14 is carried by a knob shaft 14A having a lower end 14A' threadably engaging a threaded bore 14B of cap 41 so that counter-clockwise rotation of shaft 14A by knob 14 moves shaft 14 upward to allow the piston assembly 40 to move upward within the chamber 40A. This vertical movement allows the heliox mixture to enter the regulator assembly where its pressure is regulated according to variations in the pressure of seal 52 of inlet fitting 32 and the mixture is then dispensed to the patient through fitting assembly 13.

Inlet fitting 32 directly beneath seal 52 allows heliox to enter the regulator at a controlled rate. Inlet fitting 32 is that described in co-assigned U.S. pending application Ser. No. 10/074,877 filed on Feb. 12, 2002, by Dean et al., and is incorporated by reference herein.

When knob 14 is in the "off" position, a downward force is evenly applied by hollow stem 50 on seal 52. This constant and even force applied against seal 52 is also applied against the inlet fitting 32 and ensures that the heliox does not flow or leak into the regulator body when the system is not in use.

A bore 28 below inlet fitting 32 provides communication from inlet fitting 32 to connector fitting 10A. At the upper end of bore 28, both fill fitting 11 and rupture disk 45 communicate with bore 28.

Inlet fitting 32 has an inlet tip 51 which forms a gas tight seal when seal 52 is urged tightly against tip 51 when knob 14 is "off." An o-ring 33 (constructed of silicon as are all other o-rings in this system) surrounds hollow stem 50 at its bottom end near inlet tip 51 to prevent the heliox mixture from escaping when knob 14 is in the "off" position.

If knob 14 is turned to the "on" position, piston assembly 40 and hollow stem 50 may move upward so that the heliox mixture may pass through a space 53 by entering hollow stem 50 by means of a series of apertures 50A. The heliox mixture is communicated through hollow stem 50 and to a space 53 directly above piston assembly 40. This creates a downward force on piston assembly 40 which is counterbalanced by a spring 36 of music wire which pushed upward on piston assembly 40. The heliox mixture in tank 2 is at a high pressure of 500–2200 PSIG enters body 10 and is regulated by this counter balancing of forces. The heliox now at a relatively low pressure flows through the system preferably in the range of 10 liters per minute plus or minus 1 liter per minute when the system is in the "on" position in the single outlet regulator. In the double outlet regulator the Heliox flows at a rate of 18 liters per minute plus or minus 2 liters per minute.

Knob shaft 14A also contains TORX® screw 18 which extends into knob shaft 14A from knob 14. The knob is secured by a washer 18A and seated beneath TORX® screw 18.

To prevent accidental or inadvertent operating of knob 14, a pull pin 15 extends vertically through knob 14 into cap 41 at a location radially outwardly from the knob's center and is secured by a spring mechanism 39. A pull ring 15B extends through the head of pull pin 15 to permit the user to extract the pull pin 15 for enabling use of the system. A lanyard 23 connects pull pin ring 15B to body 10 in order to prevent pin 15 from being misplaced after the pull pin is pulled.

Figure 5:
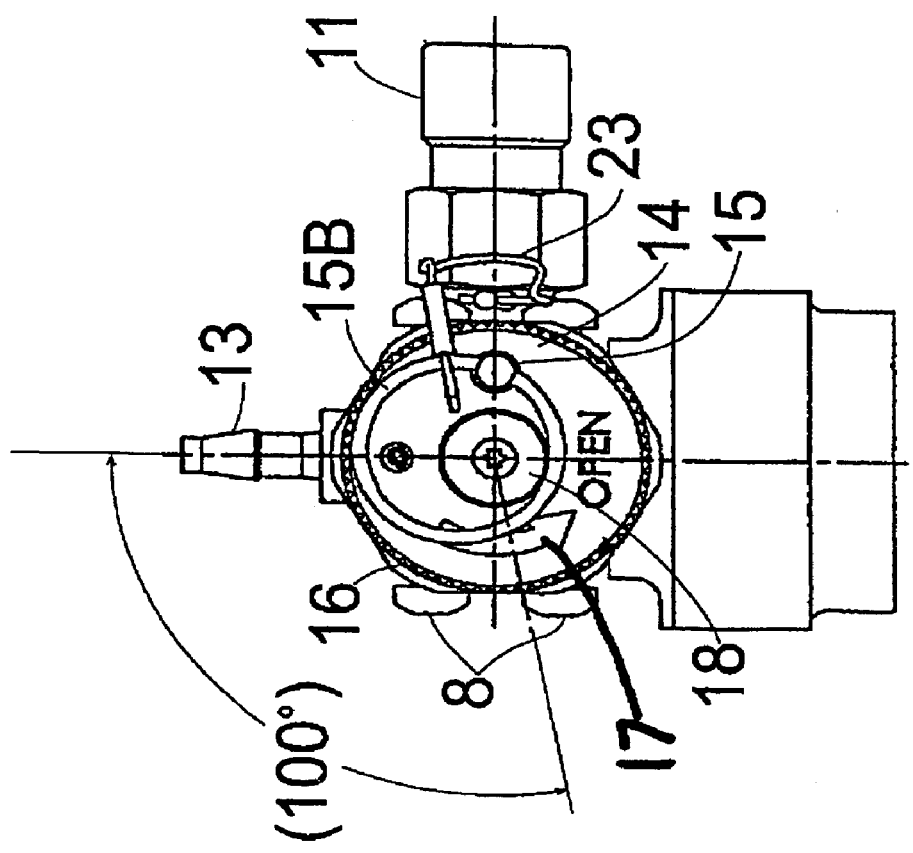
FIG. 5 is a top plain view of a control valve of the regulator.

Referring to FIG. 5, knob 14 has a knurled grip 16 to aid in turning the knob. A directional indication 17 shows the user that knob 14 should be turned only in a counter-clockwise direction.

Figure 6:
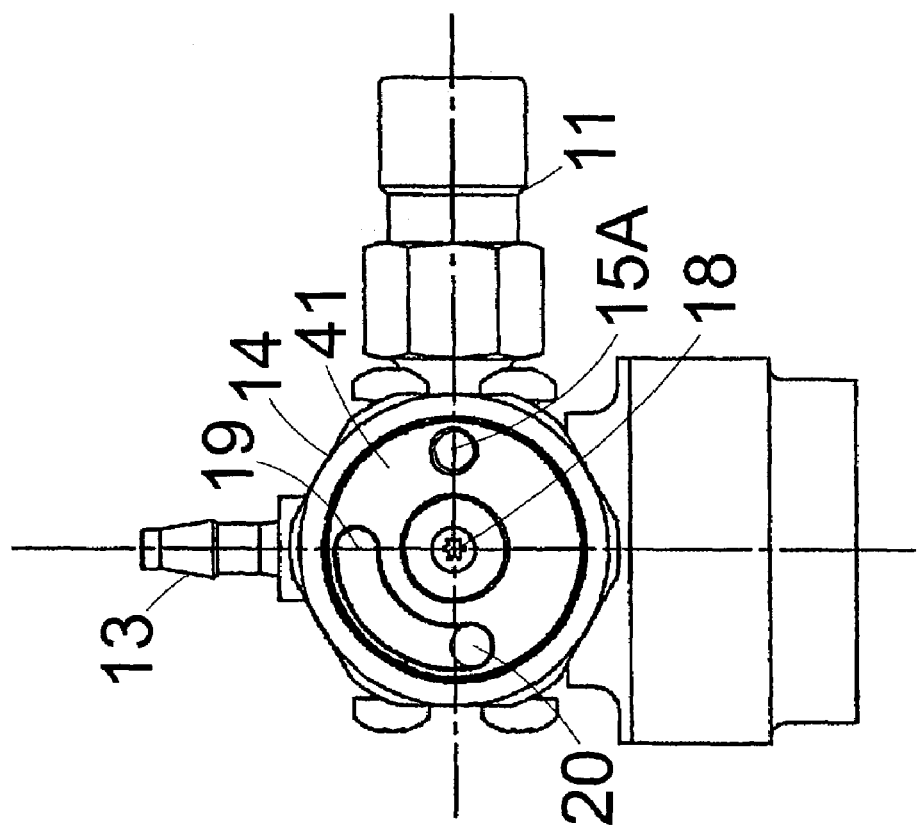
FIG. 6 is a bottom plain view of the control valve of FIG. 1 of the regulator.
Figure 7:
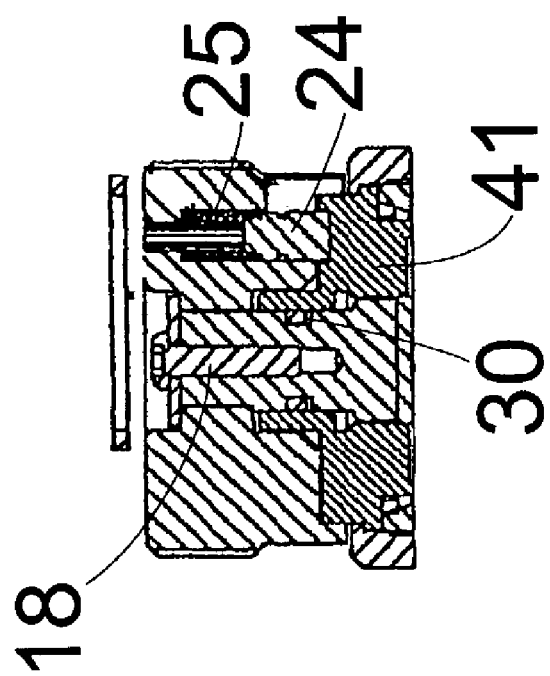
FIG. 7 is a vertical cross sectional view of the top section of the regulator as taken along line 7—7 of FIG. 1.

FIGS. 6 and 7 show the underside of knob 14 and a cross section of the upper portion of body 10 in greater detail. An o-ring 30 seals knob shaft 14A within cap 41.

Detent lock 24, preferably of a Nylatron® material is directly above cap 41 and below knob 14, is explained in greater detail below. Cap 41 has an arcuate slot 19 molded into its topside concentric with the axis of the cap. Slot 19 extends in a 100 degree arc from its starting point to its ending point, at which is formed a recess 20 in cap 41 such that as the knob reaches its "on" position detent lock 24 is propelled into recess 20 by spring 25.

Detent lock 24 thus allows the knob to become locked into the "on" position. More specifically, spring 25 exerts a downward motion on detent lock 24 propelling it away from knob 14 and towards cap 41 and body 10. When the knob is in the "off" position, detent lock 24 rests in slot 19 and is freely moveable thereon upon movement of knob 14 from the "off" position. As knob 14 is turned to the "on" position, detent lock 24 travels in slot 19 until knob 14 is rotated 100 degrees. At that point, detent lock 24 is forced downward into recess 20 of cap 41 by spring 25 to lock the device in the "on" position until reset by specializing resetting tool 3.

Figure 8:
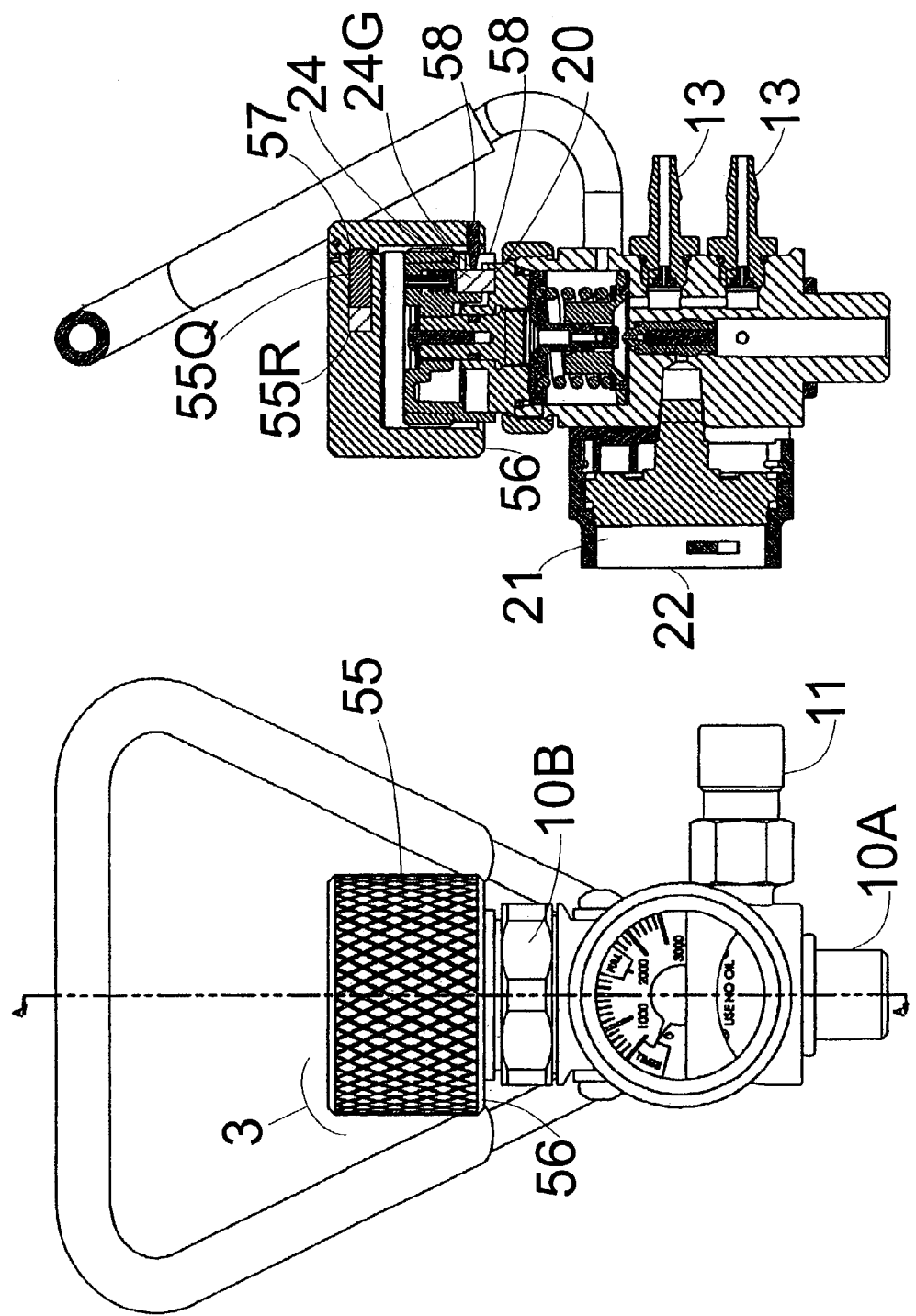
FIG. 8 is perspective and cross sectional view of the regulator with the special resetting tool in place.

FIG. 8 shows regulator 10 with resetting tool 3 on the top side of body 10 covering knob 14 when in use. Resetting tool 3 is generally possessed by an authorized entity such as a service center technician or reconditioning facility. Resetting tool 3 is cylindrical and hollow and designed so as to be able to cover knob 14 when in use. Resetting tool 3 includes a cup-like body 55 having a side wall 56 with a knurled exterior surface and further includes a swingable side wall portion 57 carrying a horizontal pin member 58.

Side wall portion 57 is pivotally affixed to body 55 by a pivot 55Q and is urged radially outward by a compression spring 55R acting against a pin 55Q. When pressed radially inward side wall portion 57 moves horizontal pin member 58 radially inward to engage detent lock 24, which preferably has an annular grove 24G which the tip of prior members 58 can engage.

Thus, when side wall portion 57 is pressed inward, horizontal pin member 58 is forced to engage detent lock 24. Then, by slightly raising tool 3 upward, detent lock 24 is lifted out of recess 20 to allow knob 14 to be turned back clockwise to the "off" position by clockwise turning of tool 3.

Various other resetting tools are possible, such as devices having a blade sized for detent lock 24 to enable it to be raised for unlocking the knob allowing it to be rotated to its "off" position.

In use, system A is operated quickly and easily through a sequence of steps. First, a mask or nasal cannula (not shown) is connected to body 10 by tubing 13T is fitted to the patient. Next, the patient or user assisting the patient quickly removes pull pin 15 with enough force to extract it from knob 14. Pull pin 15 remains tethered to body 10 by lanyard 23. The patient (or another assisting the patient) easily turns knob 14 in a counter clockwise motion to the "on" position. While the patient is wearing a mask or cannula a therapeutic heliox mixture from tank 2 is allowed to flow through the regulator at a constant and controlled rate described above.

Flow continues until all the heliox in tank 2 is expended because knob 14 is locked into the "on" position. This provides a single, uninterrupted, dose of beneficial heliox to the patient to aid breathing. The locked "on" position of knob 14 assures that the flow will beneficially be continuous and cannot be interrupted even though the patient may have lessening of symptoms until a treatment facility can be reached.

An authorized service entity is equipped with resetting tool 3 and uses the tool to reset knob 14. Tank 2 is refilled with fresh heliox through fill fitting 11.

The embodiment was chosen and described to best explain the principals of the invention an its practical application to thereby enable others skilled in the art to best utilize the invention in various embodiments and with various modifications as are suited to the particular use contemplated.

As various modification could be made in the constructions and methods herein described and illustrated without departing from the scope of the invention, it is intended that all matter contained in the foregoing description or shown in the accompanying drawings shall be interpreted as illustrative rather than limiting.

What is claimed is:

1. A device for providing a single dose administration of a gaseous mixture having therapeutic benefit when received by a patient but posing risk to the patient if interrupted prematurely, comprising:
   an apparatus to provide a regulated flow of a gaseous mixture comprising;
   a flow initiation control selectively operable by the patient or other user for initiating the regulated flow; and
   a lock associated with the flow initiation control for preventing discontinuation of said flow by the patient once initiated to assure that the flow will beneficially be continuous and cannot be interrupted by the patient, the flow initiation control being resettable only by use of a resetting tool by an authorized person other than the patient.

2. A device as set forth in claim 1 wherein said gaseous mixture comprises 80 percent helium and 20 percent oxygen with substantially no other elements present.

3. A device as set forth in claim 1 further comprising a carrying means for lifting and carrying the device.

4. A device as set forth in claim 3 wherein said carrying means is a color coded handle to indicate that said device is to be used to administer a particular type of gaseous mixture.

5. A device as set forth in claim 1 wherein said apparatus to provide a regulated flow of a gaseous mixture includes a one piece inlet fitting.

6. A device as set forth in claim 1 further including at least one means for the gaseous mixture to exit the device for delivery to the patient.

7. A device as set forth in claim 1 further including a pressure relief device permitting the gaseous mixture to escape if the pressure of said gaseous mixture reaches a pre-determined level.

8. A device as set forth in claim 1 wherein the device includes a storage tank for containing the gaseous mixture, the device further including a refill connection to refill a storage tank when said storage tank is connected to said device.

9. A device as set forth in claim 1 further including a means for indicating pressure of the gaseous mixture in a storage tank which is attached to said device to contain the gaseous mixture.

10. A system for providing single dose administration of a gaseous mixture having therapeutic benefit when received by a patient but posing risk to the patient if interrupted prematurely, comprising in combination:
    a storage tank containing the gaseous mixture;
    a regulator device in communication with the storage tank for receiving the gaseous mixture to supply it to the patient at a flow rate providing therapeutic benefit to the patient for so long as there is the gaseous mixture in the storage tank, the regulator device including
        a flow initiation control selectively operable by the patient or other user for initiating said flow; and
        a lock for preventing discontinuation by the patient of said flow once initiated to assure that the flow will beneficially be continuous and cannot be interrupted by the patient; and
    a tool selectively operable with the regulator device by an authorized person for resetting the flow initiation control.

11. The system as set forth in claim 10 wherein said gaseous mixture is a heliox mixture comprising helium and oxygen.

12. The system as set forth in claim 11 wherein said heliox mixture is comprised of 80% helium and 20% oxygen without any substantial amount of another gas.

13. A system for providing single dose administration of a gaseous mixture having therapeutic benefit when received by a patient but posing risk to the patient if interrupted prematurely, comprising in combination:
    a storage tank containing a gaseous mixture;
    a regulator device in communication with the storage tank for receiving the gaseous mixture to supply it to the patient at a flow rate providing therapeutic benefit to the patient for so long as there is the gaseous mixture in the tank, the regulator device including:
    a knob assembly for initiating the flow of said gaseous mixture and capable of rotating about a set axis by activating a mechanism that allows the gaseous mixture to flow at a constant, regulated pressure through the regulator device to the patient;
    a detent lock attached to the knob assembly preventing the knob assembly from being turned to an "off" position after the knob assembly is turned to an "on" position;
    the knob assembly being resettable only by use of a resetting tool for the detent lock by an authorized person other than the patient;
    a pull pin device inserted through the knob assembly to prevent the knob from being turned to an "on" position until the pull pin device is removed by the patient or other user;
    a gauge to display the pressure of the gaseous mixture in the pressure vessel, the gauge being carried by the regulator device; and
    a carrying handle attached to the exterior surface of the regulator device for carrying the system.

14. A system for providing single dose administration of a gaseous mixture having therapeutic benefit when received by a patient but posing risk to the patient if interrupted prematurely, comprising in combination:
    a storage tank containing the gaseous mixture;
    a regulator device in communication with the storage tank for receiving the gaseous mixture to supply it to the patient at a continuous and regulated flow rate providing therapeutic benefit to the patient for so long as there is the gaseous mixture in the storage tank, the regulator device including
        a flow initiation control selectively operable by the patient or other user for initiating said flow; and
        a lock for preventing discontinuation of said flow once initiated; and
        a mechanism designed to prevent entry of said gaseous mixture into the regulator device by exerting a constant and even pressure over a sealing member when said system is not in use; and
    a tool selectively operable with the flow control device by an authorized person for resetting said flow initiation control.

15. A method of operating a system according to claim 10 comprising the steps of:
    a) connecting a means for delivering the gaseous mixture between the system and the patient;
    b) operating the flow initiation control to initiate the flow so that the gaseous mixture flows through the regulator device to the means for delivering;
    c) continuing delivery of the gaseous mixture until all of the gaseous mixture in the storage tank flows through the regulator until exhausted.

16. The method of claim 15 further comprising the step of using a resetting tool selectively co-operable with the regulator device for disengaging the locking means and returning the flow initiation control to the "off" position.

17. The method of claim 15 further comprising the step of refilling the storage tank with said gaseous mixture after the flow initiation control is returned to the "off" position.

18. A method of operating a device according to claim 1 comprising the steps of:
    a) connecting a means for delivering to the patient the gaseous mixture from the device;
    b) operating the flow initiation control until the lock is engaged whereby to lock the control into the "on" position then;
    c) continuing delivery of the gaseous mixture until all of the gaseous mixture has been delivered to the patient or until medical assistance can be attained for the patient.

* * * * *